(12) United States Patent
Peck et al.

(10) Patent No.: US 9,891,227 B2
(45) Date of Patent: Feb. 13, 2018

(54) ULTRASENSITIVE DETECTION OF A BIOLOGICAL TARGET BY APTAMER-CONJUGATED GOLD NANOPARTICLES

(71) Applicant: Academia Sinica, Taipei (TW)

(72) Inventors: Konan Peck, Taipei (TW); Pan-Chyr Yang, Taipei (TW); Yi-Chung Chang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 170 days.

(21) Appl. No.: 14/701,267

(22) Filed: Apr. 30, 2015

(65) Prior Publication Data

US 2015/0316545 A1 Nov. 5, 2015

Related U.S. Application Data

(60) Provisional application No. 61/987,683, filed on May 2, 2014.

(51) Int. Cl.
*G01N 33/53* (2006.01)
*G01N 33/58* (2006.01)
*G01N 33/543* (2006.01)
*G01N 33/569* (2006.01)

(52) U.S. Cl.
CPC ....... *G01N 33/585* (2013.01); *G01N 33/5308* (2013.01); *G01N 33/54326* (2013.01); *G01N 33/54333* (2013.01); *G01N 33/56938* (2013.01)

(58) Field of Classification Search
USPC .......... 435/6.12, 91.1, 287.1, 6.15, 6.1, 6.11, 435/91.31; 506/9, 30; 536/23.1, 24.3, 536/24.5; 424/9.1; 359/32
See application file for complete search history.

(56) References Cited

U.S. PATENT DOCUMENTS

| | | | | |
|---|---|---|---|---|
| 2008/0241843 A1* | 10/2008 | Zare | .......................... | G01J 3/02 435/6.12 |
| 2010/0330702 A1* | 12/2010 | Savran | ................. | C12Q 1/6804 436/518 |
| 2015/0005188 A1* | 1/2015 | Levner | ................. | C12Q 1/6837 506/9 |
| 2015/0056627 A1* | 2/2015 | Karkkainen | ....... | A61K 31/7088 435/6.15 |
| 2016/0348112 A1* | 12/2016 | Ochsner | ............. | G01N 33/5308 |

OTHER PUBLICATIONS

Chang et al (Scientific Reports, vol. 3, No. 1863, pp. 1-7 (2013).*
Maeng et al (J. Nanoscience and Nanotechnology, vol. 12, pp. 5138-5142 (2012).*
Jin-Soo Maeng, Namsoo Kim, Chong-Tai Kim, Seung Ryul Han, Young Ju Lee, Seong-Wook Lee, Myung-Hyun Lee, and Yong-Jin Cho. Rapid Detection of Food Pathogens Using RNA Aptamers-Immobilized Slide Journal of Nanoscience and Nanotechnology vol. 12, 5138-5142, 2012.
Yi-Chung Chang, Chia-Ying Yang, Ruei-Lin Sun, Yi-Feng Cheng, Wei-Chen Kao, and Pan-Chyr Yang. Rapid single cell detection of Staffolococcus aureus by aptamer-conjugated gold nanoparticles. Scientific Reports May 3:1863, 2013.

* cited by examiner

*Primary Examiner* — Jane Zara
(74) *Attorney, Agent, or Firm* — Hsiu-Ming Saunders; Intellectual Property Connections Inc.

(57) ABSTRACT

Methods of assaying a biological target are disclosed. The method comprises: (a) providing a sample containing the biological target; (b) providing biotin-labeled first aptamers conjugated to a gold nanoparticle (GNP), and second aptamers conjugated to a magnetic bead, wherein the first and the second aptamers exhibit specific binding affinities to the target; (c) incubating the sample with the first and the second aptamers to obtain target-bound aptamers; (d) separating the target-bound aptamers from unbound aptamers; (e) eluting the first aptamers from the GNP; (f) incubating the eluted biotin-labeled first aptamers with streptavidin-magnetic beads and reporter gold nanoparticles (GNPs) to obtain a complex comprising: the bead, the first aptamers, attached to the bead; and the reporter GNPs captured by the bead through the first aptamers; (g) eluting the reporter GNPs captured; and (h) detecting the target by measuring and analyzing a light-scattering signal of the eluted reporter GNPs.

16 Claims, 3 Drawing Sheets

ULTRASENSITIVE DETECTION OF A BIOLOGICAL TARGET BY APTAMER-CONJUGATED GOLD NANOPARTICLES

REFERENCE TO RELATED APPLICATION

The present application claims the priority to U.S. Provisional Application Ser. No. 61/987,683, filed May 2, 2014, which is herein incorporated by reference in its entirety.

FIELD OF THE INVENTION

The present invention relates generally to detection of a biological target in a sample, more specifically to detection of an analyte by aptamer-conjugated gold nanoparticle.

BACKGROUND OF THE INVENTION

*Staphylococcus aureus* is a facultative anaerobic, Gram-positive bacterium discovered by Dr. Alexander Ogston in 1880. Literature reports suggest that about 30% to 50% of the population has been carriers of *S. aureus* at one time in their lives and about 20% are long-term carriers. *S. aureus* is widespread in the environment and has become one of the most commonly isolated pathogens in hospital-acquired infections. Moreover, *S. aureus* can cause numerous illnesses, from minor skin infections to life-threatening diseases, such as abscesses, pneumonia, meningitis, endocarditis, and septicemia. According to reports of the National Institutes of Health and Centers for Disease Control and Prevention, *S. aureus* infects 500,000 people yearly in America, more than 94,000 of which are cases of life-threatening, antibiotic-resistant *S. aureus* infections.

Bacterial culture and metabolic tests are standard protocols for bacterial identification in use by most hospitals. But this process might take days for identification of the pathogenic bacteria—an unacceptable delay in emergency and critically ill situations such as sepsis. For this reason, several ultrasensitive detection methods based on nucleic acid amplification, such as PCR (polymerase chain reaction), LCR (ligase chain reaction) and SDA (strand displacement amplification), among others, have been introduced. All of these technologies are capable of detecting low numbers of bacterial cells within several hours. However, these technologies require prior isolation of bacterial DNA, preparation of enzyme reaction mix, and expensive instruments for nucleic acid amplification. These high costs and complex procedures limit the widespread use of these technologies for clinical diagnosis. Antibody-based immunoassays for bacterial identification are well established and have been used for many years. However, ultrasensitive detection with such approaches is limited by the fact that antibodies are proteins and thus cannot be amplified. This limitation was circumvented by the development of a technology called immuno-PCR, in which the antibody is cross-linked with a DNA "barcode" for PCR amplification. Although this technology is sensitive, the conjugation and purification of antibody-DNA complexes is still a daunting task.

Aptamers are DNA or RNA molecules that can fold into a variety of structures. Like an antibody, a good aptamer can specifically bind to its target with pico- to nanomolar affinity. Importantly, unlike antibodies, aptamers can be directly amplified by PCR. Since their discovery in the late 1990s, aptamers have been widely used in many applications, including target detection, enzyme inhibition, receptor regulation, and drug delivery. Several bacterial aptamers had been isolated and recently used in identification of bacteria, including *Escherichia coli, Mycobacterium tuberculosis, Salmonella enterica*, and *Bacillus anthracis*. However, none of these studies reported showed the capability of identifying extremely low numbers of target bacteria without a PCR reaction.

Therefore, a heretofore unaddressed need exists in the art to address the aforementioned deficiencies and inadequacies, especially in connection with detection of a biological target present in a low concentration in a sample.

SUMMARY OF THE INVENTION

In one aspect, the invention relates to an ultrasensitive method of assaying a biological target, comprising:
(a) providing a sample containing the biological target;
(b) (i) providing a plurality of biotin-labeled first aptamers, the biotin-labeled first aptamers being conjugated to a gold nanoparticle; and
   (ii) providing a plurality of second aptamers, the second aptamers being conjugated to a magnetic bead, wherein the biotin-labeled first aptamers and the second aptamers exhibit specific binding affinities to the biological target;
(c) incubating the sample with the biotin-labeled first aptamers and the second aptamers to obtain biological target-bound aptamers:
(d) separating the biological target-bound aptamers from unbound aptamers;
(e) eluting the biotin-labeled first aptamers from the gold nanoparticle in the biological target-bound aptamers to obtain eluted biotin-labeled first aptamers unconjugated to the gold nanoparticle;
(f) incubating the eluted biotin-labeled first aptamers unconjugated to the gold nanoparticle with a plurality of streptavidin-magnetic beads and a plurality of reporter gold nanoparticles to obtain a complex comprising:
   (i) the streptavidin-magnetic bead;
   (ii) the biotin-labeled first aptamers, attached to the streptavidin-magnetic bead; and
   (iii) the reporter gold nanoparticles, each of which being attached to one of the biotin-labeled first aptamers and captured by the streptavidin-magnetic bead through the biotin-labeled first aptamers;
(g) eluting the reporter GNPs captured by the streptavidin-magnetic bead from the complex; and
(h) detecting the biological target by measuring and analyzing a light-scattering signal of the eluted reporter gold nanoparticles.

In one embodiment of the invention, the detecting step comprises exciting the reporter gold nanoparticles with a laser to generate the light-scattering signal of the reporter gold nanoparticles.

In another embodiment of the invention, the exciting step is performed by employing a 638-nm laser light source.

The second aptamers may be amino-labeled and covalently conjugated to the magnetic bead. The magnetic beads may be epoxy beads.

In one embodiment of the invention, the detecting step comprises:
(i) converting the light-scattering signal generated into an electrical signal;
(ii) amplifying the electrical signal;
(iii) reading the electrical signal with a voltmeter; and
(iv) measuring and analyzing the read electrical signal.

In another embodiment of the invention, each of the gold nanoparticles are coated with a thiol-DNA adaptor and the biotin-labeled first aptamers are conjugated to the gold nanoparticles by annealing to the thiol-DNA adaptors.

The detecting step may further comprise calculating the concentration of the biological target in the sample by comparing the measured signal to a standard curve from a known sample.

The incubating step may further comprise the step of separating the reporter gold nanoparticles captured by the streptavidin-magnetic bead from uncaptured reporter gold nanoparticles.

In another embodiment of the invention, the step of eluting the reporter gold nanoparticles captured by the streptavidin-magnetic bead from the complex comprises the step of adding a base to the complex.

The step of eluting the biotin-labeled first aptamers from the gold nanoparticle may comprise the step of heating the biological target-bound aptamers to a temperature of no less than 90° C.

In another embodiment of the invention, the biological target is a bacterium. The bacterium may be *Staphylococcus aureus*.

In another embodiment of the invention, the biotin-labeled first aptamers and the second aptamers each have 54 to 68 nucleotides in length and comprise nucleotide sequences that are at least 90% identical to SEQ ID NO: 1 and 2, respectively.

In another embodiment of the invention, the biotin-labeled first aptamers and the second aptamers comprise the nucleotide sequences of SEQ ID NOs: 1 and 2, respectively. The aptamers each may comprise a loop sequence of $_{48}C_{49}C_{50}A_{51}C_{52}C_{53}G$.

In another embodiment of the invention, the sample contains no more than 10 bacterial cells.

In another embodiment of the invention, the biological target is selected from the group consisting of a biological cell, a virus, an analyte, and a protein.

Further in another embodiment of the invention, the separating step is performed by employing a magnetic force.

In another aspect, the invention relates to an ultrasensitive method of assaying a biological target, comprising:
(a) providing a sample containing the biological target;
(b) providing a plurality of gold nanoparticles, each of the gold nanoparticles being conjugated with a plurality of aptamers that exhibit a specific binding affinity to the biological target;
(c) incubating the sample containing the biological target with the plurality of the gold nanoparticles conjugated with the plurality of aptamers to obtain biological target-bound gold nanoparticles;
(d) removing unbound gold nanoparticles;
(e) eluting the gold nanoparticles from the biological target in the biological target-bound gold nanoparticles; and
(f) detecting the biological target by measuring and/or analyzing a light scattering signal of the gold nanoparticles eluted from the biological target,
wherein the biological target is *Staphylococcus aureus*.

In another aspect, the invention relates to an ultrasensitive method of assaying a biological target, comprising:
(a) providing a sample containing the biological target;
(b) providing a plurality of aptamers that exhibit a specific binding affinity to the biological target, wherein the aptamers are each labeled with a biotin or a fluorescent molecule;
(c) incubating the sample containing the biological target with the plurality of the aptamers to obtain biological target-bound aptamers;
(d) removing unbound aptamers; and
(e) detecting the biological target by performing the following steps:
  (i) measuring a fluorescence signal of the biological target-bound aptamers, wherein the aptamers are each labeled with a fluorescent molecule; or
  (ii) (a') incubating the biological target-bound aptamers with fluorescently labeled streptavidin, wherein the aptamers are each labeled with a biotin molecule, to obtain a complex; and
  (b') removing unbound fluorescently labeled streptavidin; and
  (c') measuring a fluorescence signal of the complex, which are labeled with fluorescently labeled streptavidin,
wherein the biological target is *Staphylococcus aureus*, and the aptamers each have 54 to 68 nucleotides in length and comprise a nucleotide sequence that is at least 90% identical to SEQ ID) NO: 1 or 2.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1A:
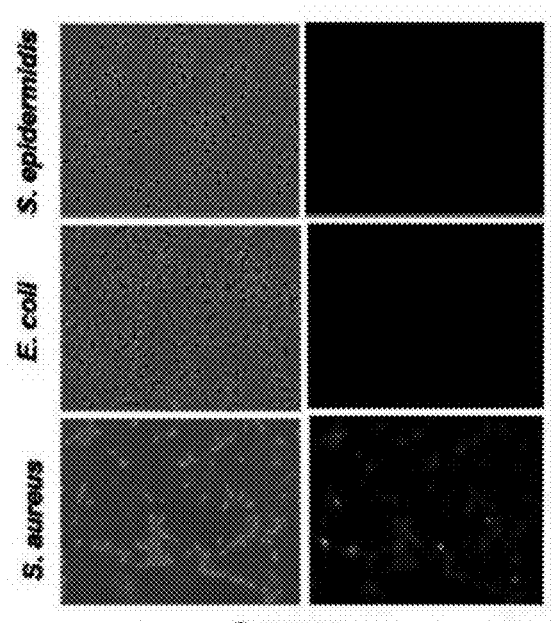
FIGS. 1A-C show the results of characterization of light-scattering signals of GNPs. (A) Fluorescence microscopic detection of SA17 binding to different bacteria. Biotin-labeled SA17 (500 nM) was incubated with *S. aureus* cells at 4° C. for 30 minutes and stained with streptavidin-PE. Bright field (left) and fluorescent (right) images of each of the tested bacterial strains are shown. (B) SEM images (50,000× enlargement) show the interaction of aptamer-GNPs and *S. aureus*. Top panel: interaction of SA17-coated 60- or 100-nm aptamer-GNPs and *S. aureus*; Bottom panel: absence of interaction of 60-nm aptamer-GNPs with *S. epidermis* and *E. coli*. (C) Quantification of IFA results showing interactions of SA17 and SA61 with 21 bacterial strains. FAM-labeled SA17 or SA61 (500 nM) were incubated with 100 μl suspensions of different bacterial strains ($OD_{600}$=1) at 4° C. for 30 minutes. Bound aptamers were eluted and analyzed using a florescence reader.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, an "analyte" is a target of interest that can specifically interact with (bind to) an aptamer and be detected and/or measured.

Aptamers are single-stranded DNA or RNA (ssDNA or ssRNA) molecules that can bind to pre-selected targets including proteins and peptides with high affinity and specificity.

```
SA-17
                                      (SEQ ID NO: 1)
TCCCTACGGCGCTAACCCCCCCAGTCCGTCCTCCCAGCCTCACACCGCCA

CCGTGCTACAA;

SA-61
                                      (SEQ ID NO: 2)
TCCCTACGGCGCTAACCTCCCAACCGCTCCACCCTGCCTCCGCCTCGCCA

CCGTGCTACAA.
```

There is an unmet demand of new platform technology to improve bacterial detection and identification in clinical practice. In this study, we developed a rapid, ultra-sensitive, low cost, and non-polymerase chain reaction (PCR)-based method for bacterial identification. Using this method, which measures the resonance light-scattering signal of aptamer-conjugated gold nanoparticles, we successfully detected single S. aureus cell within 1.5 hours. This new platform technology may have potential to develop a rapid and sensitive bacterial testing at point-of-care.

Gold nanoparticles (GNPs) are gold particles that range in size from 1 nm to several hundred nanometers and possess strong light-scattering properties. The intensity of light scattering is based on the size of the particle. Moreover, GNPs can be easily conjugated with protein or modified DNA molecules through sulfhydryl linkages. These properties make GNPs a useful tool for ultrasensitive molecular detection. Moreover, a GNP-based amplification method has been developed and the system was shown to be capable of detecting prostate-specific antigen with sensitivity in the attomolar range. In the current study, we determined the resonance light-scattering intensity of different sizes and concentrations of GNPs in a liquid-phase system under 638 nm diode laser beam stimulation. *S. aureus*-targeting aptamers were identified by cell-based SELEX (Systematic Evolution of Ligands by Exponential Enrichment), and dissociation constants and binding specificity were characterized. Two of the isolated aptamers. SA17 and SA61, recognized *S. aureus* with high specificity and nanomolar affinity. Using these aptamers, we developed a rapid, ultra-sensitive, low cost, and non-PCR-based method that combines aptamer-conjugated GNPs and a resonance light-scattering-detection system. In this method, the number of SA17 and SA61 aptamers or aptamer-conjugated GNPs bound to single *S. aureus* cells is quantified by quantitative PCR (qPCR). For ultrasensitive detection of *S. aureus* cells, aptamers are conjugated onto GNPs followed by bead-based amplification. After amplification, one bacterial cell was capable of generating more than $10^4$; GNPs, and amplified GNPs could be detected by the light-scattering-sensing system. Single cell detection was reached within 1.5 hours without expensive equipment such as thermal cyclers or centrifuges.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Primers and Aptamers. A ssDNA library composed of 30-nucleotide (nt) long, randomized probe sequences flanked by 16-nt PCR priming sequences at both 5'- and 3'-ends (TCCCTACGGCGCTAAC (SEQ ID NO: 3)-[N]$_{30}$-GCCACCGTGCTIACAAC (SEQ ID NO: 4)) was synthesized by Integrated DNA Technologies (Coralville. Iowa, USA). All other primers and aptamers were from Purigo Biotech (Taipei, Taiwan). The bacteria-bound probes isolated during the SELEX process were amplified by PCR primers (designated R9 primers) with the sequences 5'-TCC CTA CG CGC TAA C-3' (forward: SEQ ID NO: 5) and 5'-GTT GTA GCA CGG TGG C-3' (reverse; SEQ ID NO: 6). Proper folding of aptamers was attained by denaturing at 95° C. for 2 minutes followed by gradual cooling to 37° C. at a rate of 2° C. per 40 seconds using a thermocycler. The aptamers were then stored at −20° C. until ready for assay. Biotin-labeled aptamers were used for phycoerythrin (PE)-staining and fluorescence microscopy. See Chang et al. "Rapid single cell detection of *Staphylococcus aureus* by aptamer-conjugated gold nanoparticles" Sci Rep. 2013; 3:1863, which is incorporated herein by reference in its entirety.

Cell-Based SELEX. A total of $10^7$ *S. aureus* (ATCC: 6538DR) cells were incubated in SELEX buffer with an aptamer library containing $10^{15}$ randomized DNA sequences for 30 minutes on ice. After washing away the unbound aptamers, bound aptamers were eluted with SELEX buffer and heated at 95° C. for 2 minutes. The isolated aptamers were refolded by thermal cycling, as described above, and counter-selected with $10^8$ *S. epidermidis* cells on ice for 30 minutes. The supernatant was collected and PCR-amplified with R9 forward primers and biotin-labeled R9 reverse primers in PCR buffer containing 50 mM NaCl, 10 mM Tris-HCl (pH 8.9), 10 mM betaine, 1% dimethyl sulfoxide, 200 μM each dNTP, 1 mM MgCl$_2$, 200 nM each primer, and 2 units of Taq DNA polymerase. The PCR amplicons were rendered single-stranded and purified with streptavidin-coated magnetic microspheres (Chemogen, So. Portland, Me., USA). The isolated ssDNA pool was refolded and incubated with a new batch of *S. aureus* to start a new SELEX round.

Bacterial Cultures and Harvest Conditions. All bacteria were purchased from Food Industry Research and Development Institute (FIRDI, Hsin-Chu, Taiwan). The bacterial strains used in the study were *B. subtilis* (ATCC: 21336), *C. freundii* (ATCC: 8090), *E. coli* (ATCC: 43896), *K. pneumonia* (ATCC: 13883), *L. monocylogenes* (ATCC: 19112), *M. catarrhalis* (ATCC: 25238), *P. aeruginosa* (ATCC: 27853), *S. enteric* (ATCC: 13314), *S. boydii* (ATCC: 8700), *S. flexneri* (ATCC: 29903), six strains of *S. aureus* (ATCC: 6538DR, 6538P, 12600, 25923, 29213, 6538), *S. epidermidis* (ATCC: 155), *S. maemolyticus* (ATCC: 29970), *S. saprophyticus* (ATCC: 15305), *S. boris* (ATCC: 43077) and *S. pneumoniae* (ATCC: 6301), *Staphylococcus* spp. were cultured with Brain-Heart infusion broth (Oxoid, Basingstoke, England) at 37° C.; *B. subtilis* was cultured with LB broth (Difco, Detroit. Mich., USA); the remaining bacteria were cultured with nutrient broth (Difco, Mich., USA). The concentration of *S. aureus* was determined by serial dilution with subsequent plating on agar plates and measurement of colony forming units (CFUs). CFUs were also determined by measuring optical density (OD) at 600 nm (an OD$_{600}$ of $1.0 \approx 1.5 \times 10^9$ CFU/ml). Muller-Hinton broth (Difco) was used in antimicrobial susceptibility testing.

Measurement of $K_d$s for SA Aptamers. *S. aureus* cells were incubated with serially diluted aptamers for 30 minutes at 4° C. with gentle shaking. The bacteria were washed with 3×SELEX buffer by centrifugation. Bound aptamers were eluted with 95° C. distilled H$_2$O (dH$_2$O) and mixed with SYBR Green Master Mix containing 200 nM R9 primer pair, qPCR was performed using an ABI-7900 system (Applied Biosystems, Alameda. Calif. USA). K was calculated according to the equation, $Y=B_{max} \times X/(K_d+X)$.

Immunofluorescence Assay. FAM-labeled SA aptamers (250 nM) were incubated with 100 μl of bacterial suspension with an OD$_{600}$ of 1.0. The mix was incubated on ice for 30 minutes and washed several times with SELEX buffer to remove unbound aptamers. To avoid interference due to autofluorescence of bacterial cells, bound aptamers were eluted by heating, and eluates were analyzed using a SpectraMAX PLUS fluorescence microplate reader (Molecular Devices, Union City. Calif., USA).

Conjugation of GNPs. Adaptor sequences (A$_{20}$) were conjugated onto GNPs (BBInternational, Cardiff, UK) by adjusting the pH of the gold colloid solution to 8.5-9.1 using 100 mM K$_2$CO$_3$ and incubating overnight at 25° C. with 5 μM thio-labeled adaptor sequences, pre-activated with 10 mM tris(2-carboxyethyl)phosphine (TCEP). After the adaptor sequences had been conjugated, NaCl was added to a final concentration of 200 mM. Unbound adaptor sequences were removed by washing six times with adaptor-GNPs with stabilizing buffer containing 20 mM Tris-HCl (pH 8.5), 1% bovine serum albumen (BSA), 5 mM KCl, 1 mM CaCl$_2$, 2 mM MgCl$_2$ and 150 mM NaCl by centrifugation. The adaptor-GNPs were stored at 4° C. GNPs were conjugated with aptamer sequences by incubating 10 μM aptamer sequences (with poly-T linker) with 1 ml of adaptor-GNP solution containing $10^{10}$ particles. The mixture was then heated to 65° C. for 5 minutes, gradually cooled to 4° C. at a rate of 2° C. per 40 seconds using a thermocycler, and incubated overnight at 4° C. Aptamer-GNPs were washed six times with stabilizing buffer and stored at 4° C. before use.

Aptamer-GNPs for the Detection of *S. aureus*. For the direct detection of *S. aureus*, $10^8$ aptamer-GNPs were incubated with bacteria samples in 25 μl of SELEX buffer (40 mM HEPES buffer pH 8.0, 5 mM KCl, 1 mM $CaCl_2$, 2 mM $MgCl_2$, and 150 mM NaCl). After washing away the unbound aptamer GNPs using a 0.45-μm filter column (Millipore, Billerica, Mass. USA), bound aptamer-GNPs were eluted with 0.1 M NaOH and quantified using the light-scattering-detection system. For bead amplification, M270 beads were coated according to the manufacturer's instructions. Briefly, $10^8$ M270 epoxy beads (Invitrogen, Carlsbad, Calif., USA) were incubated with 1 mole of amine-labeled SA17 for 48 hours in pH 9.0 borate buffer. After blocking with 1% BSA, the coated M270 beads were stored in stabilizing buffer at 4° C. Then, $10^8$ biotin-SA61-GNPs and $10^7$ SA17-M270 were incubated with bacterial samples for 30 minutes on ice. After separation with a magnet, bound biotin-SA61 was eluted with 95° C. $dH_2O$. Streptavidin-Magnetic beads (Chemogen) were blocked with hybridization buffer (20 mM Tris-HCl pH 9.0, 1% BSA, 100 mM NaCl) for 1 hour at 37° C. and then incubated with $10^8$ adaptor-GNPs and previously eluted biotin-aptamers for 30 minutes at 37° C. The GNPs captured by magnetic beads were eluted with 0.1 M NaOH and analyzed using the light-scattering-detection system.

For single cell detection, *S. aureus* was inoculated in Brain heart infusion media and incubated at 37° C. for expansion. Bacterial cells were collected while $OD_{600}$ reached 0.5-0.8. The collected cells were repetitively resuspended by pipetting and washed twice by SELEX buffer containing 2% of PEG 2000 and 0.02% of TWEEN®-20 to reduce cell aggregates. Bacterial cells were resuspended to 1 $OD_{600}$ with SELEX buffer containing 1% of BSA and 0.02% of TWEEN®-20. The cell density of $1OD_{600}$ was determined by plate count. The cell suspension was further serially diluted to one cell per μl. The 10 μl diluted bacterial suspensions containing approximately ten bacterial cells was confirmed by plate count and bead-based amplification assay simultaneously. In bead-based amplification assay, 10 μl of diluted suspension was further diluted to 300 μl and equally divided into 30 wells. Each well was further analyzed by bead-based amplification to determine whether it contained bacteria or not. The positive wells were recorded and served as containing one bacteria cell each.

Scanning Electron Microscopy. For SEM observations, bacteria were incubated with $10^8$ 60-nm aptamer-GNPs or $10^7$ 100-nm aptamer-GNPs at 4° C. for 30 minutes. The mixtures were filtered using a 0.45-μm filter column and spotted onto a poly-L-lysine-coated cover glass to allow bacterial attachment (10 minutes at 4° C.). The samples were fixed by incubating with 1% formaldehyde and 2% glutaraldehyde at room temperature for 2 hours, then postfixed with 2% osmium tetroxide for 1 hour, dehydrated with ethanol, critical-point dried, and coated with gold-palladium alloy. Finally, bacterial surfaces were photographed using a Jeol JSM T330A scanning electron microscope (Jeol, Inc., Peabody. Mass., USA) at 15 kV acceleration.

Results

To identify specific aptamers against *S. aureus*, we developed a cell-based method based on SELEX, as described in Chang et al. Supplementary FIG. S1. The details of the protocol are described in Chang et al. Supplementary Information. Briefly. $10^7$ *S. aureus* cells were first incubated with an aptamer pool and bound aptamers were isolated after washing five times. After removing non-specific aptamers, bound aptamers were refolded and incubated with $10^8$ *Staphylococcus epidermidis* for counter-selection. Like *S. aureus*, *S. epidermidis* is a common flora on human skin and belongs to the same genus as *S. aureus*. We hypothesized that if the isolated aptamer could distinguish *S. aureus* from *S. epidermidis*, it might target a specific structure of *S. aureus* and should therefore not cross-react with bacteria from other genera. The aptamers that survived counter-selection were amplified and purified as single-stranded DNA (ssDNA) aptamers. Purified ssDNA aptamers were added into a fresh batch of *S. aureus* cells to start the next SELEX round. After eight rounds of SELEX, the pool was cloned and sequenced. The dendrogram of the isolated sequences is shown in Chang et al. Supplementary FIG. S2 and complete sequence information is presented in Chang et al. Supplementary Table 1. Aptamer clones SA17 and SA61 were selected for their high specificity and relatively strong total binding signal against *S. aureus*.

Figure 1B:
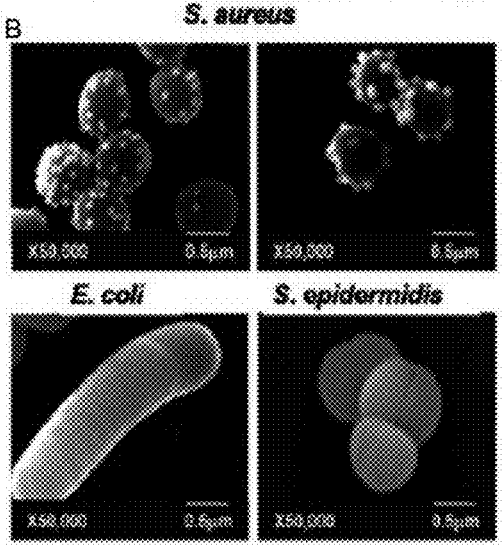
Figure 1C:
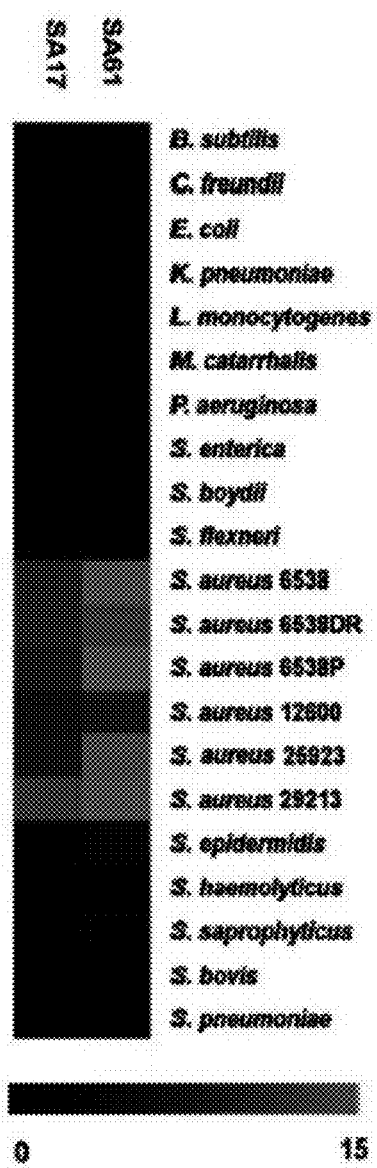

The specific binding of SA17 and SA61 was verified by fluorescence microscopy (FIG. 1A) and scanning electron microscopy (SEM) (FIG. 1B), and quantified in immunofluorescence assays (IFAs) (FIG. 1C). Other than weak IFA signals in assays of SA61 with *S. epidermidis* and *P. aeruginosa* (FIG. 1C), SA17 and SA61 did not cross-react with 13 other bacterial species, including *Bacillus subtilis. Citrobacter freundii, E. coli, Klebsiella pneumoniae, Listleria monocytogenes, Moraxella catarrhalis, Salmonella enterica, Shigella boydii, Shigella flexneri, Streptococcus bovis Streptococcus pneumoniae Staphylococcus saprophyticus*, and *Staphylococcus haemolyticus* (FIG. 1, also see Chang et al. Supplementary FIG. S3, and Supplementary Table 2). We also analyzed six different *S. aureus* strains (ATCC: 6538, 6538DR, 6538P, 12600, 25923, 29213) for their interactions with SA17 and SA61 in IFAs. The results indicated that SA17 and SA61 were able to recognize all six strains of *S. aureus* (FIG. 1C). Although SA61 cross-reacted with *S. epidermidis* and *P. aeruginosa*, these interactions were significantly weaker than those with *S. aureus* strains. The successful detection of all six *S. aureus* strains by SA17 and SA61 suggested that these aptamers might be capable of very high detection rates in tests of clinical *S. aureus* samples. The results of qPCR, which was also used to study the binding specificity, were consistent with IFA findings (data not shown). The affinities of SA17 and SA61 for *S. aureus* cells, measured as dissociation constants ($K_d$s), were determined using a qPCR-based total binding assay (see Chang et al. Supplementary FIG. S4a). The results showed that the $K_d$s of SA17 and SA61 aptamers for *S. aureus* cells were 35 and 129 nM, respectively. The secondary structures of SA17 and SA61, predicted by mfold software, are shown in Chang et al. Supplementary FIG. S4b. Immobilization of the aptamers on GNPs might alter the aptamer functional structure. For this reason, the affinities of SA17-GNPs and SA61-GNPs for *S. aureus* must be re-evaluated. The result showed that the $K_d$s of SA17-GNPs and SA61-GNPs for *S. aureus* were 3.03 and 9.9 nM, respectively, a significant enhancement compared to the free aptamer forms (see Chang et al. Supplementary FIG. S4c). We also estimated the number of SA17 and SA61 molecules bound to single *S. aureus* cells by qPCR. The results showed that 900 to 1200 molecules of SA17 and 1500 to 2300 molecules of SA61 bound a single *S. aureus* cell (see Chang et al. Supplementary FIG. S5). Collectively, these data suggest that one bacterium can generate thousands of DNA sequences and, unlike immuno-PCR, these sequences can directly serve as a DNA barcode for detection.

Figure 2A:
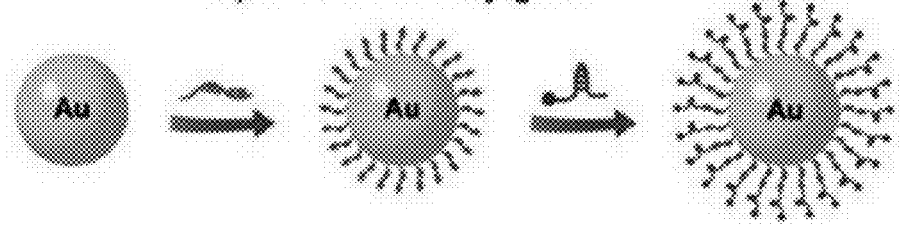
FIGS. 2A-C show a flowchart of *S. aureus* detection using aptamer-conjugated GNPs. (A) Aptamers were conjugated onto 60-nm GNPs with thio-DNA adaptors. (B) Aptamer-GNPs in the direct detection of *S. aureus*. $10^9$ aptamer-GNPs were incubated with *S. aureus* cells. After removal of unbound aptamer-GNPs, bound aptamer-GNPs were eluted and their light-scattering signals were analyzed. (C), Bead-based amplification in the detection of *S. aureus*. SA61-aptamers (biotin-aptamer 1) were conjugated onto 60-nm GNPs, and SA17-aptamers (aptamer 2) were conjugated onto magnetic beads. Aptamer 1-GNPs and aptamer 2-magnetic beads interacted with *S. aureus* and the resulting complexes were isolated with a magnet. Bound biotin-aptamer 1 was eluted by heating and further incubated with an excess of reporter-GNPs (conjugated with DNA adapter) and streptavidin (SA)-coated magnetic beads. The reporter-GNPs were then captured with SA-magnetic beads in the presence of biotin-aptamer 1. The bound reporter-GNPs were eluted with NaOH and their light-scattering signals were analyzed.

Two strategies were used for detecting the interaction between aptamer-GNPs and *S. aureus*: a direct detection method and a bead-amplification method (FIG. 2). For both methods, SA17 and SA61 aptamers were first conjugated to 60-nm GNPs by a thio-modified adaptor sequence (FIG. 2A).

Figure 2B:
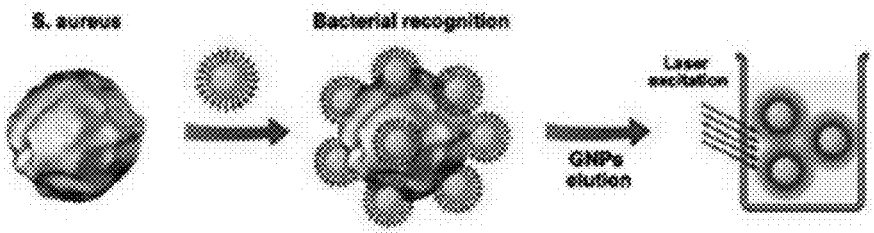
Figure 2C:
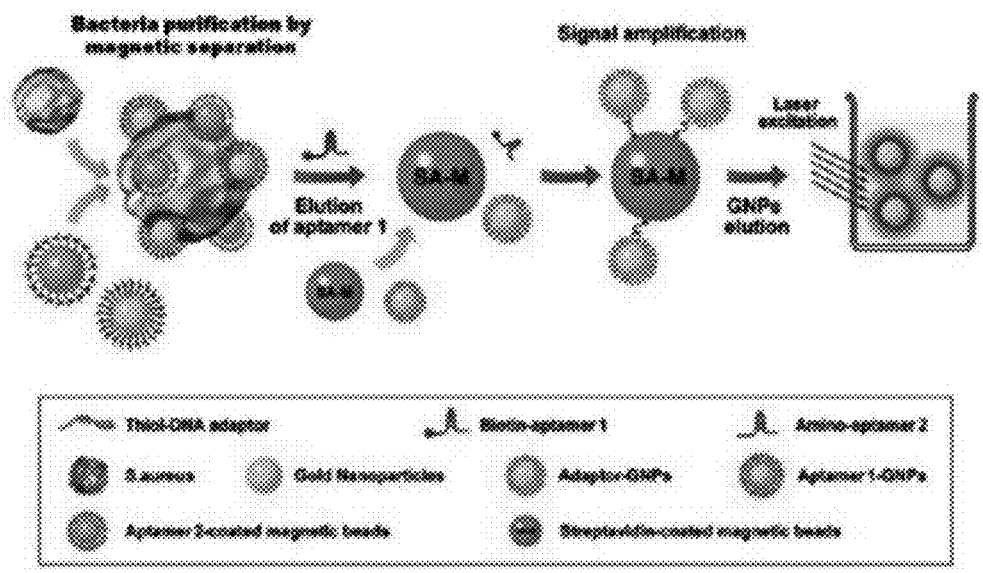

The aptamer-GNP-binding capacity of a single bacterial cell was then analyzed directly using a binding assay based on size separation employing 0.22-μm filters, as shown in FIG. 2B. In this assay, the aptamer-GNP complex was incubated with different numbers of *S. aureus* cells for 30 minutes on ice. After washing away the unbound aptamer-GNPs, bacteria-bounded GNPs were eluted by NaOH and collected for the analysis of resonance light-scattering signals (see below).

In the bead-based amplification method for *S. aureus* detection (FIG. 2C), magnetic beads were pre-coated with SA17 (SA17-MAGs), and 60-nm GNPs were pre-coated with dual biotin-labeled SA61 (b-SA61-GNPs). The SA61 aptamer was selected for conjugating with GNPs because of its higher binding capacity for *S. aureus* compared to SA17. SA17-MAG and b-SA61-GNPs were incubated with *S. aureus* cells and separated by a magnet. After removing the unbound b-SA61-GNPs, the b-SA61 sequences coated onto beads were eluted and incubated with adaptor-GNPs and streptavidin-MAG. The b-SA61 aptamer acts as a bridge that allows adaptor-GNPs to be captured by streptavidin-MAG, increasing the total number of GNPs for the detection system. The total duration from amplification to detection was 1.5 hours. With this amplification method, one aptamer-GNP can generate 1500 aptamer sequences (see Chang et al. Supplementary FIG. S6), resulting in the amplification of the number of GNPs by several orders of magnitude.

Figure 3A:
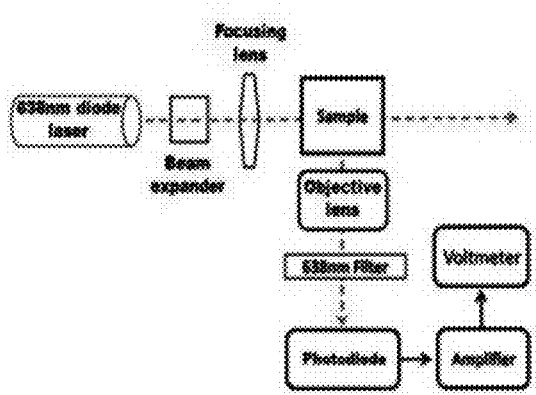
FIGS. 3A-D illustrate a light-scattering system and application of aptamer-GNPs in the detection of S. aureus. (A) A schematic diagram of the instrument. The instrument consists of a 638-nm diode laser for excitation, an objective lens for collection of scattered-light signals, and a photodiode for transducing the light into electrical signals. The data are collected with a voltmeter. (B) Results of direct detection of S. aureus using SA17-GNPs and SA61-GNPs. The numbers of bacteria tested in the study were $10^4$ and 2-fold serial dilutions in selection buffer. In this study, SA17 and SA61 aptamers were conjugated with 60-nm GNPs ($10^7/\mu l$). Filled diamond: SA61-GNPs incubated with S. aureus; filled square: SA17-GNPs incubated with S. aureus; filled triangle: SA61-GNPs incubated with S. epidermidis; filled inverted triangle: SA17-GNPs incubated with S. epidermidis. (C) Results of bead-based amplification in the ultrasensitive detection of S. aureus. The starting number of bacteria was $10^3$ followed by 2-fold serial dilutions. Biotin-SA61 (b-SA61)-conjugated 60-nm GNPs ($10^7/\mu l$) and SA17-conjugated magnetic beads ($5 \times 10^6/\mu l$) were incubated with S. aureus for 30 minutes. Bound b-SA61 aptamers were eluted and incubated with SA-magnetic beads and reporter-GNPs. Reporter-GNPs were eluted and analyzed for light-scattering signal. Filled circle: S. aureus; filled square; S. epidermidis. (D) Results of single bacterial cell detection. The number of bacterial cells was determined by plate count and bead-based amplification. The mean bacteria numbers were 13.5 and 14.3, respectively. Two assay platforms show good correlation with $R^2$ of 0.89.
Figure 3C:
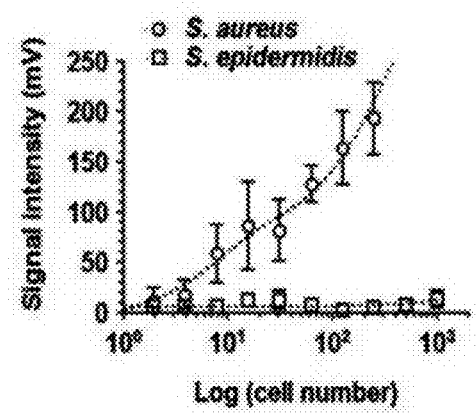
Figure 3B:
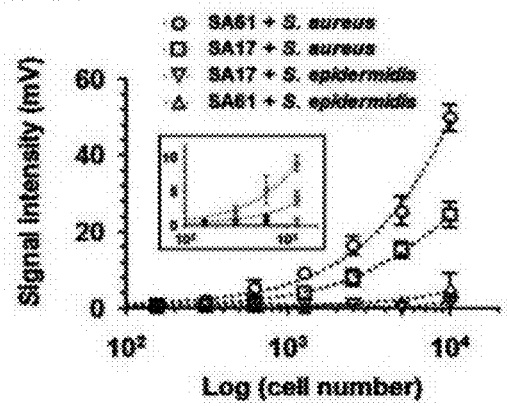

To investigate the possibility of using the resonance light-scattering property of GNPs in ultrasensitive bacterial detection, we constructed an instrument consisting of a 638-nm laser light source, an objective lens, a photodiode, an amplifier and a digital voltmeter, as described in FIG. 3A. Samples containing GNPs are excited by 638-nm laser, and the generated resonance light-scattering signals are converted into an electrical signal by the photodiode. The electrical signals are further amplified by an amplifier and read by the voltmeter. Chang et al. Supplementary FIG. S7a shows the light-scattering signal of $3 \times 10^5$ 60-nm GNPs/μl with serial 2-fold dilutions. The light-scattering intensities increased linearly with GNP concentration (Chang et al. Supplementary FIG. S7b) and exponentially with the sixth power of the particle radius (Chang et al. Supplementary FIG. S7c). This result is consistent with the previous finding that the light-scattering intensity of GNPs is enhanced with increases in GNP size[27]. The lower limit of detection of the instrument was $63 \pm 21$ GNPs/μl for 100-nm particles and $508 \pm 176$ GNPs/μl for 60-nm particles. At these levels, SA17- and SA61-GNPs could detect as few as 312 and 1250 bacterial cells, respectively (FIG. 3B). Particle numbers were quantified from light-scattering signals in FIG. 3B by reference to the standard curve of 60-nm GNPs shown in Chang et al. Supplementary FIG. S7b. The equation was: particle numbers/μl=(signal intensity $-10.913) \times 10^3$. According to the equation, a single bacterial cell could bind 14.5 molecules of SA17- or 35.5 molecules of SA61-conjugated 60 nm-GNPs, respectively. The relative sizes of GNPs and *S. aureus* cells are shown in SEM images (FIG. 1B). Tests of samples containing extremely low numbers of bacteria revealed that analysis of light-scattering signals following the amplification procedure shown in FIG. 2C was able to detect as few as 10 bacterial cells (FIG. 3C). However, at dilutions approaching a single bacterium, variations in detection were significant, possibly reflecting the unequal distribution of bacterial cells in the solution during the dilution process.

Figure 3D:
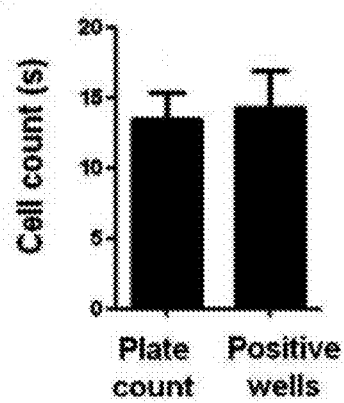

For accurately demonstrating if this bead-based amplification system could detect as few as single bacterial cell, *S. aureus* suspension was serially diluted and plate counted revealing that 1 $OD_{600}$ of suspension contained $1.5 \times 10^8$ cells/mi. Ten bacterial cells roughly estimated by optical density was further determined by plate count and bead-based amplification assay. The suspension containing approximately 10 bacteria cells was divided into 30 independent samples. After analyzed by bead-based amplification assay, the positive samples were marked and served as containing one bacterial cell each (Chang et al Supplementary FIG. S8b). In four independent assays, the cell numbers determined by the bead-based amplification assay and plate-count method were 11:12, 16:19, 11:8 and 16:18. The $R^2$ for the results of two assays was 0.89. These data were combined and are shown in FIG. 3D.

A number of molecular technologies had been developed for bacterial detection. However, few have been widely used in clinical applications, primarily because of the associated high costs and complex protocols, which are cumbersome for the clinical operator. Most rapid and sensitive technologies, such as qPCR and the Verigene system, are based on the detection of bacterial DNA. Detection of bacterial DNA requires bacterial cell lyses, which is a laborious and time-consuming process, especially for Gram-positive bacteria such as *S. aureus* that required lysostaphin to breakdown the thick cell wall. Moreover, unlike bacterial surface antigens, which are numerous, the number of DNA targets is limited. This difference in copy numbers can be several orders of magnitudes, and higher target numbers suggest a lower limit of detection. Immuno-PCR is a technology that can ultra-sensitively detect bacterial surface antigen using an antibody chimera with a DNA barcode. However, conjugating DNA molecules onto a specific site of an antibody without affecting its interaction can be problematic. Moreover, immuno-PCR requires an expensive qPCR machine for amplification and analysis of the sample.

In summary, DNA aptamer and GNPs technology were combined to demonstrate an ultrasensitive bacteria detection system. *S. aureus*, a well-known human pathogen, was chosen for aptamer selection. Aptamers that specifically recognize *S. aureus* were identified, and an ultrasensitive method for rapid bacterial detection was developed that uses aptamer-conjugated GNPs. A determination of the $K_d$s of free aptamer forms and aptamer-GNPs fir *S. aureus* showed that the $K_d$s of aptamers were significantly enhanced upon conjugation with GNPs. This increased affinity might be caused by an avidity effect reflecting multiple aptamers and targets interactions. Using aptamer-GNPs, we developed a bead-based amplification method for detecting *S. aureus*, and demonstrated that it is capable of rapidly detecting single bacterial cells. Despite a large variation in the signal intensity in this assay, a statistical analysis confirmed a strong correlation between the bead-based amplification assay and the traditional plate-count method. This signal variation might be caused by cell aggregation, which is a common phenomenon among *Staphylococcus* species.

Using this ultrasensitive method, we achieved PCR-like sensitivity and quantified bacterial numbers within 1.5 hours without the need for any expensive instruments. The protocol is simple and the cost of the method is low. This new platform technology may have potential for development as a rapid and sensitive multiplex detection system for common pathogens in clinical settings such as intensive care units. Taken together, these advantages make this technology an appealing choice for future development of point-of-care pathogen testing.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. An ultrasensitive method of assaying a biological target, comprising:
   (a) providing a sample containing the biological target;
   (b) (i) providing a plurality of biotin-labeled first aptamers, the biotin-labeled first aptamers being conjugated to a gold nanoparticle; and
   (ii) providing a plurality of second aptamers, the second aptamers being conjugated to a magnetic bead, wherein the biotin-labeled first aptamers and the second aptamers exhibit specific binding affinities to the biological target;
   (c) incubating the sample with the biotin-labeled first aptamers and the second aptamers to obtain biological target-bound aptamers;
   (d) separating the biological target-bound aptamers from unbound aptamers;
   (e) eluting the biotin-labeled first aptamers from the gold nanoparticle in the biological target-bound aptamers to obtain eluted biotin-labeled first aptamers unconjugated to the gold nanoparticle;
   (f) incubating the eluted biotin-labeled first aptamers unconjugated to the gold nanoparticle with a plurality of streptavidin-magnetic beads and a plurality of reporter gold nanoparticles to obtain a complex comprising:
   (i) the streptavidin-magnetic bead;
   (ii) the biotin-labeled first aptamers, attached to the streptavidin-magnetic bead; and
   (iii) the reporter gold nanoparticle, each of which being attached to one of the biotin-labeled first aptamers and captured by the streptavidin-magnetic bead through the biotin-labeled first aptamers;
   (g) eluting the reporter GNPs captured by the streptavidin-magnetic bead from the complex; and
   (h) detecting the biological target by measuring and analyzing a light-scattering signal of the eluted reporter gold nanoparticles.

2. The method of claim 1, wherein the detecting step comprises:
   exciting the reporter gold nanoparticles with a laser to generate the light-scattering signal of the reporter gold nanoparticles.

3. The method of claim 2, wherein the exciting step is performed by employing a 638-nm laser light source.

4. The method of claim 2, wherein the detecting step comprises:
   (i) converting the light-scattering signal generated into an electrical signal;
   (ii) amplifying the electrical signal;
   (iii) reading the electrical signal with a voltmeter; and
   (iv) measuring and analyzing the read electrical signal.

5. The method of claim 1, wherein each of the gold nanoparticles are coated with a thiol-DNA adaptor and the biotin-labeled first aptamers are conjugated to the gold nanoparticles by annealing to the thiol-DNA adaptors.

6. The method of claim 1, wherein the detecting step further comprises:
   calculating the concentration of the biological target in the sample by comparing the measured signal to a standard curve from a known sample.

7. The method of claim 1, wherein the incubating step further comprises:
   separating the reporter gold nanoparticles captured by the streptavidin-magnetic bead from uncaptured reporter gold nanoparticles.

8. The method of claim 1, wherein the step of eluting the reporter gold nanoparticles captured by the streptavidin-magnetic bead from the complex comprises:
   adding a base to the complex.

9. The method of claim 1, wherein the step of eluting the biotin-labeled first aptamers from the gold nanoparticle comprises:
   heating the biological target-bound aptamers to a temperature of no less than 90° C.

10. The method of claim 1, wherein the biological target is a bacterium.

11. The method of claim 10, wherein the bacterium is *Staphylococcus aureus*.

12. The method of claim 1, wherein the biotin-labeled first aptamers and the second aptamers each have 54 to 68 nucleotides in length and comprise nucleotide sequences that are at least 90% identical to SEQ ID NO: 1 and 2, respectively.

13. The method of claim 12, wherein the biotin-labeled first aptamers and the second aptamers comprise the nucleotide sequences of SEQ ID NOs: 1 and 2, respectively.

14. The method of claim 1, wherein the sample contains no more than 10 bacterial cells.

15. The method of claim 1, wherein the biological target is selected from the group consisting of a biological cell, a virus, an analyte, and a protein.

16. The method of claim 1, wherein the separating step is performed by employing a magnetic force.

* * * * *

SEQUENCE LISTING

```
<160> NUMBER OF SEQ ID NOS: 6

<210> SEQ ID NO 1
<211> LENGTH: 61
<212> TYPE: DNA
<213> ORGANISM: Artificial Sequence
<220> FEATURE:
<223> OTHER INFORMATION: SA-17

<400> SEQUENCE: 1
tccctacggc gctaaccccc ccagtccgtc ctcccagcct cacaccgcca ccgtgctaca      60
a                                                                      61

<210> SEQ ID NO 2
<211> LENGTH: 61
<212> TYPE: DNA
<213> ORGANISM: Artificial Sequence
<220> FEATURE:
<223> OTHER INFORMATION: SA-61

<400> SEQUENCE: 2
tccctacggc gctaacctcc caaccgctcc accctgcctc cgcctcgcca ccgtgctaca      60
a                                                                      61

<210> SEQ ID NO 3
<211> LENGTH: 16
<212> TYPE: DNA
<213> ORGANISM: Artificial Sequence
<220> FEATURE:
<223> OTHER INFORMATION: probe 5'-franking sequence

<400> SEQUENCE: 3
tccctacggc gctaac                                                      16

<210> SEQ ID NO 4
<211> LENGTH: 16
<212> TYPE: DNA
<213> ORGANISM: Artificial Sequence
<220> FEATURE:
<223> OTHER INFORMATION: probe 3'-franking sequence

<400> SEQUENCE: 4
gccaccgtgc tacaac                                                      16

<210> SEQ ID NO 5
```

```
<211> LENGTH: 16
<212> TYPE: DNA
<213> ORGANISM: Artificial Sequence
<220> FEATURE:
<223> OTHER INFORMATION: PCR forward primer

<400> SEQUENCE: 5
tccctacggc gctaac                                                      16

<210> SEQ ID NO 6
<211> LENGTH: 16
<212> TYPE: DNA
<213> ORGANISM: Artificial Sequence
<220> FEATURE:
<223> OTHER INFORMATION: PCR reverse primer

<400> SEQUENCE: 6
gttgtagcac ggtggc                                                      16
```